US007575759B2

(12) United States Patent
Murphy et al.

(10) Patent No.: US 7,575,759 B2
(45) Date of Patent: Aug. 18, 2009

(54) TISSUE ENGINEERING SCAFFOLDS

(75) Inventors: William L. Murphy, Chicago, IL (US); Robert G. Dennis, Ann Arbor, MI (US); David J. Mooney, Dexter, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 620 days.

(21) Appl. No.: 10/330,578

(22) Filed: Dec. 27, 2002

(65) Prior Publication Data

US 2004/0026811 A1    Feb. 12, 2004

Related U.S. Application Data

(60) Provisional application No. 60/345,775, filed on Jan. 2, 2002.

(51) Int. Cl.
*A61F 2/00*  (2006.01)
(52) U.S. Cl. ...................................................... 424/423
(58) Field of Classification Search .................... None
See application file for complete search history.

(56) References Cited

U.S. PATENT DOCUMENTS

| | | | | | |
|---|---|---|---|---|---|
| 4,859,712 | A | * | 8/1989 | Cox ............................. | 521/62 |
| 4,902,511 | A | * | 2/1990 | Kronman .................... | 424/423 |
| 5,514,378 | A | * | 5/1996 | Mikos et al. ................. | 424/425 |
| 5,677,355 | A | * | 10/1997 | Shalaby et al. ................ | 521/61 |
| 6,103,255 | A | * | 8/2000 | Levene et al. ................ | 424/426 |
| 6,306,424 | B1 | | 10/2001 | Vyakarnam et al. .......... | 424/426 |
| 6,333,029 | B1 | | 12/2001 | Vyakarnam et al. ......... | 424/93.1 |
| 6,337,198 | B1 | * | 1/2002 | Levene et al. ................ | 435/174 |
| 6,436,426 | B1 | * | 8/2002 | Liao et al. .................... | 424/426 |
| 7,309,232 | B2 | * | 12/2007 | Rutherford et al. ........... | 433/226 |
| 2002/0005600 | A1 | * | 1/2002 | Ma .............................. | 264/49 |

OTHER PUBLICATIONS

"Humidity". Dictionary.com. Accessed online on Feb. 16, 2007. <http://dictionary.reference.com/browse/humidity>.*
Murphy et al. Salt Fusion: An approach to improve pore interconnectivity within tissue engineering scaffolds. Feb. 2002. Tissue Engineering. vol. 8, No. 1. pp. 43-52.*
Aldini, N.N., et al., "Effectiveness of a bioabsorbable conduit in the repair of peripheral nerves," *Biomaterials* 17:959-962 (1996).
Carrier et al., "Cardiac tissue Engineering: Cell seeding, cultivation parameters, and tissue construct characterization," *Biotech Bioeng* 64:580-589 (1999).
Chaignaud, B.E., et al., "The history of tissue engineering using synthetic biodegradable polymer scaffolds and cells," In: Atala,A., Mooney, D.J., eds. *Synthetic biodegradable polymer scaffolds.* Boston, MA: Birkhauser, 1997, pp. 1-14.

(Continued)

*Primary Examiner*—M P Woodward
*Assistant Examiner*—Casey S Hagopian
(74) *Attorney, Agent, or Firm*—Medlen & Carroll, LLP

(57) ABSTRACT

The present invention relates to methods and compositions for the production of scaffolds, such scaffolds to be used for a variety of purposes, including tissue engineering. More specifically, the present invention relates to the use of fused crystals, such as fused salt crystals to form a framework. The methods for producing the scaffolds of this invention improve the porosity, interconnectivity and ease of manufacture as compared to prior art methods.

16 Claims, 15 Drawing Sheets

OTHER PUBLICATIONS

Dennis et al., Excitability and isometric contractile properties of mammalian skeletal muscle constructs engineered in vitro, In Vitro Cell Dev Biol-Animal 36:327-335 (2000).

Evans, G.R.D., et al, "In vivo evaluation of poly (L-lactic acid) porous conduits for peripheral nerve regeneration," Biomaterials 20:1109-1115 (1999).

Evans, G.R.D., et al., "Tissue engineered conduits: the use of bioderadable poly(D,L-latic-co-glycolic acid) scaffolds in peripheral nerve regeneration," In: Stark, G.E., Horch, R., Tanczos, E., Eds.. Biological Matrices and Tissue Reconstruction. Berlin:Springer, (1998) pp. 225-235.

Freed et al., "Neocartilage formation in vitro and in vivo using cells cultured on synthetic biodegradable polymers," J Biomed Mater Res 27:11-23 (1993).

Harris, L.D., et al., "Open pore biodegradable matrices formed with gas foaming," J Biomed Mater Res 42:396-402, (1998).

Hutmacher, D.W., "Scaffolds in tissue engineering bone and cartilage," Biomaterials 21:2529-2543 (2000).

Ishaug-Riley et al., "Ectopic bone formation by marrow stromal osteoblast transplantation usinpoly (DL-lactic-co-glycolic acid) foams implanted into the rat mesentery," J Biomed Mater 36:1-8 (1997).

Kaufmann, P.M., et al., "Highly porous polymer matrices as a three-dimensional culture system for hepatocytes," Cell Transplant 6:463-468, (1997).

Kim et al., "Engineering smooth muscle tissue with a predefined structure," J Biomed Mater Res 41:322-332 (1998).

Lu et al., "The importance of new proccessing techniques in tissue engineering," MRS Bull 21:28-32 (1996).

Ma, P.X. and Choi, J., "Biodegradable polymer scaffolds with well-defined interconnected spherical pore network," Tissue Eng 7:23-33, (2001).

Mikos, A.G., et al. "Preparation and characterization of poly (L-lactic acid) foams" Polymer 35:10680-1077 (1994).

Murphy, W.L. and Mooney, D.J., "Controlled delivery of inductive proteins, plasmid DNA and cells from tissue engineering matrices," J Periodontal Res 34:413-419 (1999).

Murphy, W.L. et al, "Growth of continuous bone-like mineral within porous poly (lactide-co-glycolide) scaffolds in vitro," J Biomed Mater Res 50:50-58 (2000).

Murphy, W.L., et al., "Sustained release of vascular endothelial growth factor from mineralized poly(lactide-co-glycolide) scaffolds for tissue engineering," Biomaterials 21:2521-2527 (2000).

Oberpenning et al., "De novo reconstitution of a functional mammalian urinary bladder by tissue engineering," Nat Biotech 7:149-155 (1999).

Shea, L.D., et al., "DNA delivery from polymer matrices for tissue engineering," Nat Biotech 17:551-554 (1999).

Sheridan, M., et al. "Bioabsordable polymer scaffolds for tissue engineering capable of sustained growth factor delivery," J Control Rel 64:91-102 (2000).

Valentini, R.F., et al., "Collagen and laminin containing gels impede peripheral nerve regeneration through semipermeable nerve guidance channels," Exp Neurol 98:350-356 (1987).

Van Vlack, L.H. "Elements of materials science and engineering," 4ed. Addison-Wesley Publishing Company, Reading, MA, pp. 120 &316, (1980).

van Wachem et al., "Absence of muscle regeneration after implantation of a collagen matrix seeded with myoblasts," Biomaterials 20:419-426 (1999).

* cited by examiner (a)

(b)

TISSUE ENGINEERING SCAFFOLDS

This application for patent under 35 USC § 111(a) claims priority to Provisional Application Ser. No. 60/345,775 filed on Jan. 2, 2002 under USC § 111(b).

This invention was made in part with government support under grant R01-DE-13349 and training grant T32 GM 08353, both from the National Institute of Health. The government has certain rights in the invention.

FIELD OF THE INVENTION

The present invention relates to methods and compositions for the production of scaffolds to be used for tissue engineering. More specifically, the present invention relates to the control of pore structure of porous polymer scaffolds.

BACKGROUND

Tissue engineering involves the use of living cells to develop biological substitutes for tissue replacement. However, in order for tissue engineering to be practical, scaffolds must be developed that allow for tissue growth that approximates natural tissue growth.

Several techniques have been employed to develop tissue engineering scaffolds with varying degrees of success. For example, porous scaffolds composed of biodegradable polymers have found extensive use in the engineering of several tissue types (Hutmacher, D. W., "Scaffolds in tissue engineering bone and cartilage" *Biomaterials* 21:2529 2000; Chaignaud, B. E., et al., "The history of tissue engineering using synthetic biodegradable polymer scaffolds and cells" In: Atala, A., Mooney, D. J., eds. Synthetic biodegradable polymer scaffolds. Boston, Mass.: Birkhauser, 1997, pp. 1-14). Various tissue engineering strategies employ scaffolding materials as three-dimensional substrates either for in vitro cell seeding followed by transplantation (cell-based approaches), or as conductive and inductive substrates for direct implantation in vivo (conductive approaches) (Murphy, W. L. and Mooney, D. J., "Controlled delivery of inductive proteins, plasmid DNA and cells from tissue engineering matrices" *J Periodontal Res* 34:413 1999). The degree of success of these schemes depends, in part, on the internal structure of the scaffold system. Numerous applications require a highly interconnected, macroporous structure within a scaffold system to encourage neural and fibrovascular ingrowth, promote uniformity of cell seeding, and facilitate migration of both seeded cells and cells migrating from a contiguous in vivo site.

Scaffolds are built upon a framework. The framework helps regulate the interconnectivity of the scaffold material and pore size. After the scaffold is formed, the framework must be removed. Difficulties with current approaches of creating tissue engineering scaffolds referred to above include problems with consistency of final product, difficulties in regulating the scaffold interconnectivity and pore size and problems in eliminating the framework material after forming the scaffold.

What is needed is an economical method for creating functional tissue engineering scaffolds that are easy and inexpensive to produce, allow for consistency in scaffold interconnectivity and pore size and permits the easy elimination of the framework material after formation of the scaffold.

SUMMARY OF THE INVENTION

The present invention relates to methods and compositions for the production of scaffolds to be used for tissue engineering. More specifically, the present invention relates to the control of pore structure of porous polymer scaffolds.

Embodiments of the present invention generally relate to methods and compositions for the production of porous materials, including but not limited to, tissue engineering scaffolds. More particularly, embodiments of the present invention relate to compositions and methods for producing macroporous, biodegradable tissue engineering scaffolds with controlled pore interconnectivity and porosity and ease of production. Even more particularly, embodiments of the present invention relate to compositions and methods of improving processing methods for biodegradable polymers to control pore size and the extent of pore interconnection.

It is contemplated that the pores are connected (and defined in shape and size) via the fusion of fusible particulates including, but not limited to, crystals and amorphous materials. In one embodiment, the fusible particulate or particle comprises a salt porogen (e.g., salt crystals). The fusion step is contemplated to be performed prior to the formation of a three-dimensional polymer scaffold. The embodiments of the present invention are not limited to any particular salt. Any salt may be used. Although the embodiments of the present invention are not limited to any particular salt, examples of suitable salts that may be used with the present invention are calcium chloride, sodium chloride, sodium phosphate, potassium chloride, potassium phosphate, calcium phosphate and magnesium chloride. In a preferred embodiment of the present invention, sodium chloride is used.

The salt crystals of the present invention are available commercially (e.g., Mallinkrodt, Paris, Ky.). Salt crystals can be purchased in different diameter ranges and may be sieved, for example, to yield a desired size.

It is contemplated that the salt crystals of the present invention are subject to treatment conditions (e.g., humidity) for a length of time that allows the salt crystals to partially fuse together. The embodiments of the present invention are not limited to any particular percent humidity nor are they limited to any particular length of time nor any particular degree of fusion. For example, in one embodiment, the salt crystals are exposed to 50% to 100% humidity. In another embodiment, the salt crystals are exposed to 75% to 99% humidity. In yet another embodiment, the salt crystals are exposed to 92% to 98% humidity. Likewise, in one embodiment, the salt crystals are exposed to humidity for ten minutes to 48 hours. In another embodiment, the salt crystals are exposed to humidity for 12 to 36 hours. In yet another embodiment, the salt crystals are exposed to humidity for 18 to 30 hours. In yet another embodiment, the salt crystals are exposed to humidity for 22 to 26 hours.

Treatment conditions other than humidity are contemplated. For example, acids and bases and organic solvents can be used to fuse the porogen (e.g., salt crystals).

The embodiments of the present invention are not limited to any degree of fusion. One practiced in the art will recognize that the degree of fusion required for a particular purpose will vary depending on the type of cells to be cultured and the degree of interconnectivity and pore size needed. Conditions for producing different levels of fusion are described herein.

In one embodiment of the present invention, it is contemplated that a biodegradable or non-biodegradable polymer is infused into the salt crystal lattice. In another embodiment, it is contemplated that the non-biodegradable polymer is a thermoplastic. Additionally, it is contemplated that the biodegradable or non-biodegradable polymer is dissolved in a solvent to facilitate infusion. The embodiments of the present invention are not limited to any particular biodegradable or non-biodegradable polymer or solvent. A variety of biodegradable or non-biodegradable polymer-solvent combinations are contemplated by embodiments of the present invention as long as the biocompatible polymer-solvent combination does not dissolve the fused salt crystal lattice. For example, contemplated polymers include, but are not limited to, any polyester (including poly(alpha-hydroxy esters), polyethers (including polyethylene oxide), polystyrene and polymethylmethacrylate. In one embodiment, thermoplastics are contemplated for use as materials. In another embodiment, non-biodegradable polymers are contemplated for formation of the scaffold. In a preferred embodiment, the copolymer poly(lactide-co-glycolide) (PLG) is chosen due to its biocompatibility, controllable biodegradability into natural metabolites and previous use as a macroporous tissue engineering scaffold system. The polymer solvent that is used is selected for its characteristic of dissolving the polymer and for its characteristic of not being a solvent for the porogen (e.g., the salt crystals). Additionally, it is contemplated that the fused particle component (e.g., the salt framework) is removed with any solvent that does not dissolve the polymer scaffold. In a preferred embodiment, the solvent is water.

In a preferred embodiment, the present invention contemplates a method, comprising: a) providing i) a plurality of particles (e.g. fusible particulates), said particles comprising salt crystals and ii) a solution comprising a polymer (e.g. polymer dissolved or suspended in a solvent); b) exposing said particles to conditions so that said salt crystals fuse together to produce a framework (or lattice) comprising a frame and free space between said fused salt crystals; c) contacting said framework with said solution under conditions such that said solution substantially fills said free space; d) treating said solution such that said polymer forms continuous or semi-continuous a scaffold (i.e. treating so that the polymer comes out of solution and hardens); and e) removing said fused salt crystals from said scaffold (with the resulting scaffold having pores defined by the free space of the fused salt crystals used in the process). It is preferred that greater than 75% and even greater than 95% in some embodiments) of the free space is filled in step (c). The preferred treating of step (d) comprises evaporating the polymer solvent. The preferred removing of step (e) comprises dissolving said fused salt crystals. The preferred conditions of step (b) comprise exposing said salt crystals to between approximately 90% and approximately 100% relative humidity for approximately 8 to approximately 28 hours.

It is also preferred that the polymer employed be biocompatible and/or biodegradable. In one such embodiment, the present invention contemplates a method, comprising; a) providing i) a plurality of particles, said particles comprising salt crystals and ii) a solution comprising a biocompatible polymer; b) exposing said particles to sufficient humidity such that said salt crystals fuse together to produce a framework comprising a frame and free space between said fused salt crystals; c) contacting said framework with said solution under conditions such that said solution substantially fills said free space; d) treating said solution such that said polymer forms a scaffold; and e) removing said fused salt crystals from said scaffold (again, the resulting scaffold having pores).

Of course, the present invention also contemplates the scaffold (as a composition of matter) produced according to the above-described methods. In one embodiment said scaffold after step (e) comprises cells.

In one embodiment, the scaffolds of the present invention are contemplated to be used in the culture of cells and tissue. Such scaffolds of the embodiments of the present invention are not limited to a particular cell or tissue type. Any non-hemopoietic and hemopoietic tissue or cell type can be cultured on the tissue engineering scaffolds of the present invention. In one embodiment, the present invention contemplates the growth of muscular and neural cells and tissues on the tissue engineering scaffolds of the present invention.

Besides being crucial in nervous system applications, neural tissue ingrowth may be critically important in other tissues requiring sensory control, such as functional skeletal muscle, cardiac, and renal tissues. Fibrovascular ingrowth promotes mass transport to and from a developing tissue, and is particularly vital for the engineering of bulk tissues (i.e., bone, liver, skeletal muscle, etc.) in which cells do not have an avenue for procurement of oxygen and nutrients and excretion of metabolic waste. Furthermore, uniform cell seeding and facile cell migration are important to promote homogeneity of the developing tissue in conductive, inductive and cell-based tissue engineering approaches.

In other embodiments, the present invention contemplates the implantation of scaffolds into organisms without the prior addition of cells or tissue to the scaffold. In one embodiment, the scaffold is implanted and cells are allowed to migrate into the scaffold from the surrounding tissues. In another embodiment, the scaffolds are designed to encourage the migration of desired cell types and discourage the migration of undesired cell types. Cell type migration will be regulated, for example, by controlling the porosity and pore size of the scaffold or by selection of material for the construction of the scaffold. In the present invention, the porosity and the pore size of the scaffold will be controlled by selection of the particle size of the salt and the length of time and the percent humidity that the salt particles are exposed to during the construction of the frame work on which the scaffold will be constructed.

In another embodiment, the present invention contemplates scaffolds that are designed to allow the inductive migration of cells into the scaffold. For example, scaffolds are designed to release cytokines into the surrounding environment after implantation. The release of the cytokines results in the migration of specific cell types into the scaffold. In yet another embodiment, the scaffold will release plasmid DNA into the local environment thereby resulting in the transfection of large numbers of cells at localized sites.

The present invention contemplates embodiments where the porosity and pore size of the scaffold are controlled by the size of salt particle used in constructing the frame work, the percent humidity used to fuse the salt particles and the length of time the salt particles are allowed to fuse. In another embodiment, the present invention contemplates the control of pore shape and direction. For example, rectangular, square, spherical or oblong salt particles (and in some embodiments, mixtures of shapes) are used to control the shape and direction of the pores. In yet another invention, the present invention contemplates the use of solvents other than water for the formation of the salt frame. For example, solvents such as acids, bases and organic solvents are contemplated. It is also contemplated that these solvents be used to dissolve the framework after polymerization of the polymer framework. In still yet another embodiment, the heating of the salt particles, the subjecting of the salt particles to pressure and to electric or magnetic fields, are contemplated as methods for the formation of the salt framework. In still yet another embodiment, the particulate frame is subjected to directional mechanical, electrical or magnetic forces during fusion to control pore direction and pore size.

In yet another embodiment, the present invention contemplates the incorporation of, e.g., drugs, growth factors, peptides, antibodies, antibiotics, oligonucleotides, polynucleotides, etc. into the polymer framework. Although the present invention is not limited to any particular mechanism, it is believed that the incorporated substances leach out of the framework and into the local environment wherein they aid in cell chemotaxis, in the transfection of cells, in fighting disease and infection, etc. In one embodiment of the present invention, it is contemplated that methods for producing a tissue engineering scaffold involve four steps: 1) production of a salt framework to act as the porogen, 2) the introduction of a polymer solution into the salt framework, 3) the hardening of the polymer into a polymer matrix and 4) removal of the porogen from the polymer matrix leaving a tissue engineering scaffold. In one embodiment, the polymer is biodegradable.

Embodiments of the present invention contemplate: a method comprising; a) providing i) salt crystals and ii) a biodegradable polymer, b) exposing said salt crystals to conditions so that said salt crystals fuse together to produce a frame and free space, c) contacting said frame with said biodegradable polymer under such conditions so that it fills or substantially fills the free space in said frame to form a scaffold and, d) removing said frame from said scaffold.

The embodiments of the present invention also contemplate the use of calcium chloride, sodium chloride, sodium phosphate, potassium chloride, potassium phosphate, calcium phosphate and magnesium chloride salt crystals for making the frame.

The embodiments of the present invention contemplate polyester, polyethers, polystyrene, polymethylmethacrylate, and poly(lactide-co-glycolide) to be used as biodegradable polymers for the production of the scaffold. The embodiments of the present invention additionally contemplate that the polyester is poly(alpha-hydroxy ester) and the polyether is polyethylene oxide (PEO) or polyethylene glycol (PEG). In one embodiment, the biodegradable polymer is poly(lactide-co-glycolide).

It is not intended that the present invention be limited to a particular polymer or polymer source. The present invention contemplates homopolymers, copolymers and/or a mixture of polymers. In one embodiment, the polymer source is poly(L-lactic acid) (PLLA) with an inherent viscosity of approximately 1.6. In another embodiment, the polymer is poly(D,L-lactic acid-co-glycolic acid (PLGA) with an inherent viscosity of 0.5-0.6. In another embodiment, the polymer is Poly(d,l-lactic acid) (PDLLA) with a molecular weight of approximately 103,000. Said polymers are commercially available and may be purchased from Boehringer Ingelheim (Ingelheim, Germany) and/or Sigma Chemical Co. (St. Louis, Mo.). In a particular embodiment, the polymer is 85:15 poly(D,L-lactide-co-glycolide) copolymer with an inherent viscosity of 0.78. Additionally, these polymers are used without further purification.

It is also not intended that the present invention be limited to a specific solvent. In one embodiment the solvent is dioxane (D). In another embodiment the solvent is a solution of dioxane and water (D/W). In another embodiment the solvent is tetrahydrofuran (THF). In another embodiment the solvent is N,N-dimethylformamide (DMF). In another embodiment the solvent is pyridine. In another embodiment the solvent is methanol. In another embodiment the solvent is acetone. In yet another embodiment, the solvent is chloroform.

The embodiments of the present invention contemplate a method comprising; a) providing i) salt crystals and ii) a biodegradable polymer, b) exposing said salt crystals to humidity so that said salt crystals fuse together to produce a frame and free space, c) contacting said frame with said biodegradable polymer under such conditions so that it fills or substantially fills the free space in said frame to form a scaffold and, d) removing said frame from said scaffold.

The embodiments of the present invention also contemplate that the humidity used for salt crystal fusion is between approximately 90% and 100%. In one embodiment, the porogen is exposed to humidity for less than 24 hours and more preferably for less than 10 hours. In one embodiment, of the present invention also contemplates the salt crystals are exposed to humidity for approximately 20 to 28 hours. Additionally, the embodiments of the present invention contemplate that the scaffolding forming condition comprises gas foaming. Furthermore, the embodiments of the present invention contemplate that the scaffolding forming conditions comprises solvent casting.

The embodiments of the present invention contemplate a scaffold produced by; a) providing i) salt crystals and ii) a polymer, b) exposing said salt crystals to conditions so that said salt crystals fuse together to produce a frame and free space, c) contacting said frame with said biodegradable polymer under such conditions so that it fills or substantially fills the free space in said frame to form a scaffold and, d) removing said frame from said scaffold.

The embodiments of the present invention contemplate that the salt crystals are calcium chloride, sodium chloride, sodium phosphate, potassium chloride, potassium phosphate, calcium phosphate and magnesium chloride. In other embodiments, the present invention contemplates that the scaffold is made from a polymer selected from polyester, polyethers, polystyrene, polymethylmethacrylate, and poly(lactide-co-glycolide). In one embodiment, the polymer is biodegradable.

In yet other embodiments, the present invention contemplates that the polymer of the scaffold is selected from a group consisting of poly(alpha-hydroxy ester), polyether polyethylene oxide or polyethylene glycol.

The embodiments of the present invention contemplate a scaffold produced by; a) providing i) salt crystals and ii) a polymer, b) exposing said salt crystals to humidity so that said salt crystals fuse together to produce a frame and free space, c) contacting said frame with said polymer under such conditions so that it fills or substantially fills the free space in said frame to form a scaffold and, d) removing said frame from said scaffold. In one embodiment, the humidity is between approximately 90% and 100%. In another embodiment, the salt crystals are exposed to humidity for approximately 20 to 28 hours.

The embodiments of the present invention contemplate scaffolds produced by gas foaming and solvent casting.

The embodiments of the present invention contemplate a scaffold made by the embodiments of the present invention wherein the scaffold also comprises cells. The inventions not limited by the source of the cells. For example, the cells may be of any multicellular organism. In one embodiment, the cells selected from are plants and animals. In another embodiment, the cells are mammalian. In yet another embodiment, the cells are human.

One embodiment of the present invention contemplates a method, comprising; a) providing i) a plurality of particles, said particles comprising a porogen and ii) a solution comprising a polymer; b) exposing said particles to conditions so that said porogen fuses together to produce a framework comprising a frame and free space between said fused porogen; c) contacting said framework with said solution under conditions such that said solution substantially fills said free space; d) compressing said framework and solution such that a solid substance is formed; e) exposing said solid substance to high pressure gas; f) decreasing gas pressure to ambient pressure; and g) removing said fused porogen from said scaffold. In another embodiment, said method contemplates that the compression is between 100 and 2000 psi. In yet another embodiment, said method contemplates that the gas pressure is between 400 and 1200 psi. In still yet another embodiment, said method contemplates that the solid substance is a semi-solid.

DEFINITIONS

Figure 1A:
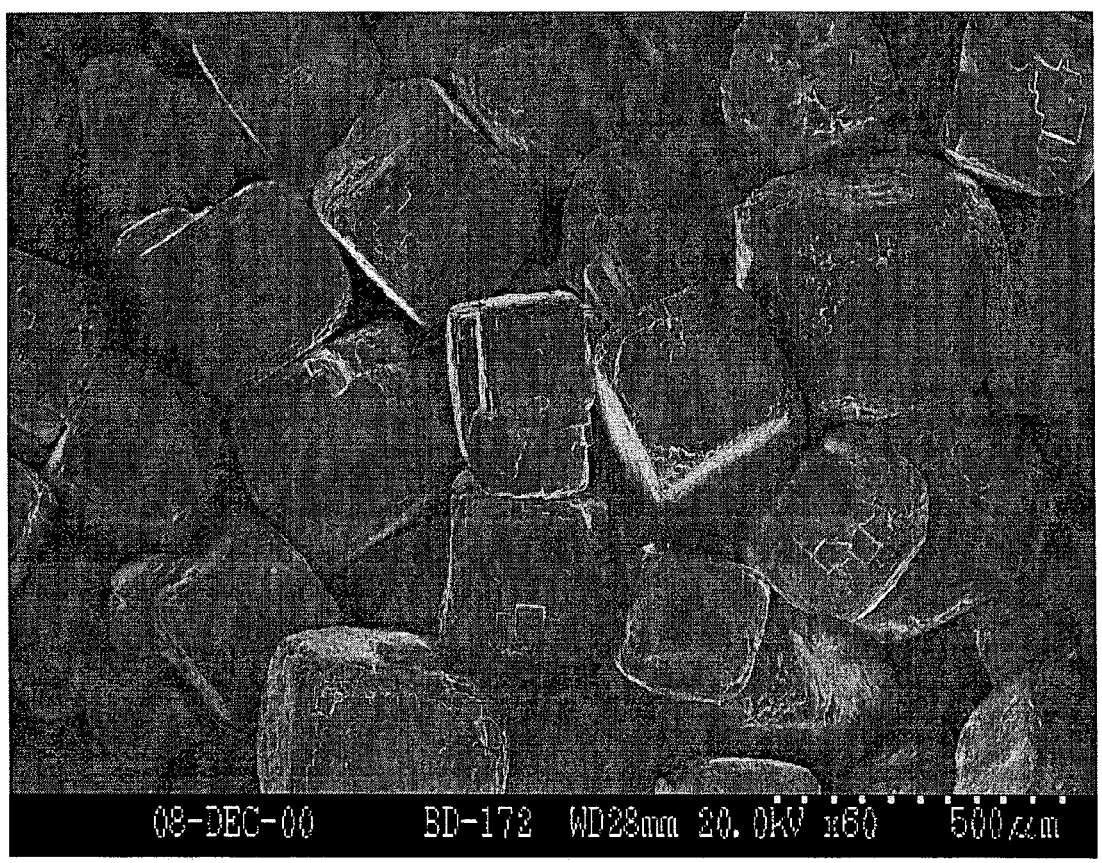
FIGS. 1a and 1b show electron micrographs of the cross section of a NaCl matrix of salt crystals fused via a) 12 hour, or b) 24 hour treatment in 95% humidity.

In order to better understand the invention, the following definitions are provided.

"Biocompatible polymer" shall be defined as a synthetic or natural material that is compatible (i.e., non-toxic) to biological systems.

"Biodegradable, biocompatible polymer" shall be defined as a biocompatible polymer that will degrade (i.e., break down) when exposed to, or placed in, a biological system. The rate of degradation is not limited in any way by the embodiments of the present invention and may be fast (e.g., degradation may take place in minutes) or slow (e.g., degradation may take place over hours, days, weeks or months).

"Salt crystal" and "salt porogen" are salt crystals that are used in embodiments of the present invention for creating a framework for the construction of polymer tissue engineering scaffolds.

"Fusion" shall be defined as the meeting and joining together. In one embodiment of the present invention, salt crystals are fused together by humidity and, sometimes heat, in the local environment or atmosphere. In another embodiment, the present invention also contemplates that the porogen (e.g., salt crystals) are fused by acids, bases or organic solvents.

"Fusible particulate" shall be defined as particles that are fused together when exposed to a condition that results in the particles melting so that when the condition that results in said melting is removed, the particles are substantially connected to each other and have free space incorporated within the fused particle matrix. Fusible particulates are approximately 0.02 mm to 5 mm across the longest measure through the particulate. Fusible particulates are made of any substance that reacts as described above. More than one type of fusible particulate may be used together.

"Semi-continuous" shall be defined, in the context of a matrix, as a martix that has portions of the matrix that are continuous (i.e., connected in two or more places) with other portions of the matrix but wherein all portions of the matrix are not required to be continuous (i.e., in connection in only one place) with other portions of the matrix.

"Humidity" and "relative humidity" shall be defined as moisture in the local atmosphere (air) of the salt crystals. Humidity measures the amount of water vapor in the atmosphere compared to the maximum amount of water vapor the air could hold at that temperature and atmospheric pressure. Air that is fully saturated with water vapor has 100% relative humidity.

"Tissue culture" and "cell culture" shall be defined as the growing of cells in sterile conditions out side of a body.

"Scaffold" shall be defined as a three dimensional structure on which cells may be grown.

"Substantially fills" shall be defined as filling an area of free space to capacity or nearly to capacity. In one embodiment, substantially fills shall mean the free space is greater than about 50% filled (e.g., filled with polymer or polymer solution). In another embodiment, substantially fills shall mean the free space is greater that about 75% filled. In yet another embodiment, substantially fills shall mean the free space is greater than about 90% filled. In still yet another embodiment, substantially fills shall mean the free space is greater than about 95% filled.

"Free space" is herein defined as the areas between the salt crystal frame (e.g., the fused porogen) embodied in the present invention. "Frame" is herein defined as a solid or semi-solid material that has open spaces (i.e., free spaces) within.

"Conductive migration" shall be defined as the migration of cells into a scaffold without the use of cytokines or other bioagents (e.g., peptides or DNA) known or suspected of inducing the migration of cells.

"Inductive migration" shall be defined as the migration of cells into a scaffold with the aid of a cytokine or other bioagents (e.g., peptides or DNA) known or suspected of inducing the migration of cells.

"Porogen" shall be defined herein as a substance that may be used to form pores in a matrix by having a polymer solution distributed throughout and amongst the porogen. Said distribution of said polymer (or polymer solution) may be before or after the porogen has fused into a framework. Said porogen may be, but need not be, a crystalline substance.

"Solvent" shall be defined as a liquid or gas (e.g., $CO_2$) holding another substance in solution. In an embodiment of the present invention, a solvent shall be a liquid that holds a polymer in solution, including but not limited to a biocompatible (and biodegradable) polymer. It is also not intended that the present invention be limited to a specific solvent. In one embodiment the solvent is dioxane (D). In another embodiment the solvent is a solution of dioxane and water (D/W). In another embodiment the solvent is tetrahydrofuran (THF). In another embodiment the solvent is N,N-dimethyl-formamide (DMF). In another embodiment the solvent is pyridine. In another embodiment the solvent is methanol. In another embodiment the solvent is acetone. In yet another embodiment, the solvent is chloroform. In still yet another embodiment, a solvent is a liquid such as water that is used to dissolve the fused salt framework into which the polymer solution is introduced and after which the polymer has hardened.

"Polymer" shall be defined herein as a macromolecule made of repeating (monomer) units or multimers. In the context of the present invention, a polymer is dissolved or suspended in an appropriate "solvent" to form a "polymer solution." In one embodiment, the polymer is allowed to polymerize by removal of the solvent. In another embodiment, removal of the solvent simply causes a phase change from liquid polymer solution to solid, continous polymer matrix.

"Polymerize" shall be defined as the creation of a chain of more than one monomer.

"Polymer solution" shall be defined herein as a solution comprising a dissolved or suspended polymer (e.g., dissolved or suspended in solvent).

"Polymer solvent" shall be defined herein as solvent into which a polymer may be dissolved but, also, will not appreciably dissolve a substance being used as a porogen.

"Thermoplastic" shall be defined as a class of polymers that melt when heated above a specified temperature, and solidify when cooled below this temperature.

"Solid," in the context of the present invention, shall be a relative term defining a measure of rigidity. The term "solid" shall include the term "semi-solid." Semi-solids shall be a solid that retains the characteristic of being malleable.

GENERAL DESCRIPTION OF THE INVENTION

The present invention relates to methods and compositions for the production of scaffolds to be used for tissue engineering. More specifically, the present invention relates to the use of sodium chloride crystals and other salts under various conditions to form a framework upon which scaffolds may (including but not limited to tissue engineering scaffolds) be constructed. However, the method of the present invention is not limited to the use of crystaline substances. Amorphous substances are also contemplated for the production of scaffolds. The novel methods for producing the tissue engineering scaffolds of this invention improve the porosity, interconnectivity and ease of manufacture as compared to prior art methods as well as to allow for greater control of these attributes.

Tissue Engineering is the growth of new connective tissues or organs, from cells on a synthetic, biodegradable scaffold to produce a partially or fully functional tissue or organ for implantation back into the donor host. In one embodiment, this technique contemplates organs to be grown from implantation (rather than transplantation) and, hence, free from immunological rejection. In another embodiment, this technique contemplates the transplantation of cells from a donor. In yet another embodiment, this technique contemplates the implantation of tissue engineering scaffolds for the migration of cells in vivo into the scaffold. In some embodiments, it is contemplated that the starting point for any tissue-engineered organ is the harvesting of small amounts of tissue from the future recipient of the tissue engineered organ. This could be as small as a 2 mm punch biopsy for some applications.

When grown on two-dimensional surfaces, the ability of cells to interact and organize themselves into functioning tissues is limited. In contrast, a three-dimensional framework allows cells to develop and assemble into tissues that more closely resemble their counterparts in the body.

In normal growth and development, the body uses specialized connective tissue cells to form "stroma" or a living matrix that provides the three-dimensional structure for each organ. Stroma also provides attachment sites and produces growth factors that promote the development of organ cells into functioning tissues. While the specific components and configuration of stroma may differ from organ to organ, the basic principle of three-dimensional stromal support applies to most organs in the body.

The procedure, in short, is to start with a scaffold, shape it as needed, seed it with living cells and bathe it with culture media and growth factors. When the cells multiply, they fill up the scaffold and grow into three-dimensional tissue, and once implanted in the body, the cells recreate their intended tissue functions. Blood vessels attach themselves to the new tissue, the scaffold dissolves, and the newly grown tissue eventually blends in with its surroundings.

In one embodiment, organ-specific cells may be seeded onto a three-dimensional scaffold in a closed bioreactor system that simulates the environment in the body. For example, in skin tissue engineering, the cells attach, divide, and secrete extracellular matrix proteins and growth factors forming a completely human, functional tissue.

Tissue engineering frequently involves stem cells, a kind of premature cell that was first isolated in 1992. Implanting stem cells in the appropriate location can generate everything from bone to tendon to cartilage since the cells will differentiate into a specific cell type according to the growth factors to which they are exposed in the culture dish or body.

Although the embodiments of the present invention are not limited to specific uses, tissue engineering scaffolds and tissue engineering may be used to recreate many tissues and organs. One example is cartilage repair. Approximately 900,000 cases of traumatic injury to articular cartilage occur annually. Adult cartilage does not normally regenerate after injury from sports and other physical injuries leading to complications. Another example is bone repair. An estimated 800,000 patients in the U.S. alone are hospitalized annually with severe bone fractures, of which half require open fracture reduction procedures. A considerable portion of these fractures do not heal properly, thus, requiring supplemental procedures, such as bone grafts. Other fractures are non-responsive to any effort but may be ideal candidates for tissue engineering. Yet another example is dermal wound healing. The failure of dermal wounds to heal properly affects an estimated 2.6 million patients in the U.S. annually. These wounds frequently are the result of complications of other conditions such as diabetes, circulation disorders and immobilization. These wounds frequently fail to heal even several months or years thereby leading to serious and life threatening complications such as infections. Often, amputation is required of the afflicted extremity.

DETAILED DESCRIPTION OF THE PREFERRED EMBODIMENTS

A. Solvent Casting and Gas Foaming.

Traditionally, tissue engineering scaffolds have been made by the solvent casting (Mikos, A. G., et al., "Preparation and characterization of poly(L-lactic acid) foams" Polymer 35:1068, 1994) and gas foaming (Harris, L. D., et al., "Open pore biodegradable matrices formed with gas foaming" J Biomed Mater Res 42:396, 1998) processes. In the solvent casting process (Mikos, A. G., et al., "Preparation and characterization of poly(L-lactic acid) foams" *Polymer* 35:1068, 1994), a polymer is dissolved in a suitable solvent, added to a porogen-containing mold and the porogen is dispersed. The solvent is then allowed to evaporate from the mixture under ambient conditions leaving a polymer matrix containing a porogen which can then be leached out in an appropriate solvent. In the gas foaming process (Harris, L. D., et al., "Open pore biodegradable matrices formed with gas foaming" J Biomed Mater Res 42:396, 1998), polymer particles are mixed with porogen particles and the mixture is compressed into a solid mixture of a discontinuous polymer with an interspersed porogen. The resulting pellet is then exposed to high pressure $CO_2$ gas, and after the pressure is allowed to equilibrate over a period of time the pressure is rapidly released causing a thermodynamic instability in the polymer component of the mixture. The instability causes the polymer to foam, and the originally discontinuous polymer particles fuse together to form a continuous polymer matrix around interspersed porogen particles, which are then leached out in a solvent. In each of these processes the degree of interconnection between pores in the resulting scaffold is determined by the interconnection of porogen particles during the solvent evaporation or polymer foaming steps, respectively. Because the porogen is dispersed within the polymer before fusion, the degree of interconnection between porogen particles is not actively controlled and the interconnectivity of pores in the final scaffold product is uncontrolled.

Enhancement in and control over porogen interconnectivity may be an important concern in various tissue engineering strategies in view of the substantial advantages of pore interconnectivity within scaffolds. Certain embodiments of the present invention solve these problems in control over scaffold porosity and interconnectivity. In a preferred embodiment of the present invention, the porogen is not dispersed. Rather, the progen is fused to create a framework (or lattice) and a polymer solution is introduced over and into this framework.

B. Cell Culture

It is not intended that the present invention be limited by the source of the cells. In one embodiment, the cells used for tissue engineering are from a biopsy. Cells from the biopsy are then cultured from explants or a collagenase digestion to create a "cell bank". These cells are then further cultured on substrates and scaffolds, under the correct physiological conditions, to form tissue-engineered constructs for implantation. The process is carried out in a tissue culture facility to maintain a sterile environment. Cellular biochemical and physical activity can be enhanced by the addition of growth factors or cytokines and also by the use of physical stimulation. In some applications, a device that applies minute physical loads stimulates the resident cell population in the scaffold into biochemical and bio-physical activity normally associated with organogenesis and tissue repair. After further tissue culture under the correct conditions, the construct can then be implanted back into the patient from whom the cells were originally removed. This technology will eliminate the need for anti-rejection drugs because the tissue engineered tissue has been grown from the patients own cells and, therefore, will be accepted as a natural part of the patients body.

C. Porogen Fusion

In an embodiment of the present invention, salt crystals can be fused via exposure to certain conditions (e.g., approximately 95% humidity), resulting in enhanced pore interconnectivity within both solvent cast and gas foamed PLG scaffolds. Fusion of a salt matrix prior to solvent casting results in formation of holes in pore walls, and the diameter and sphericity of these holes increases with increasing salt fusion treatment. Salt fusion treatment causes an increase in the compressive modulus of solvent cast scaffolds, possibly due to the formation of thick annular struts adjacent to holes in pore walls. Enhanced pore interconnectivity may be useful in a variety of tissue engineering applications, particularly those requiring intimate cell-cell contact (i.e., neural and muscular applications). Also, because the salt fusion method imparts improved pore interconnectivity in both the solvent casting and gas foaming processes, the concept may be applicable to other solid porogen-based methods for producing macro- or micro-porous material systems with high interconnectivity.

Utilization of a fused salt mold in a solvent casting, particulate leaching method results in the formation of holes between pore walls in the scaffold. With increased salt fusion time the pore structure within the scaffold cross sections became less organized. The apparent lack of an organized pore structure is due to the excellent interconnectivity of the salt fused samples, which reduces the presence of well-organized, largely closed-off pores. Upon scaffold bisection many of the pores have flattened out due to their lack of a continuous pore wall. In effect, the increased continuity of the fused salt matrix creates corresponding discontinuity in the polymer matrix, leading to large openings between pores and superior interconnectivity. Additionally, intact samples could not be fabricated using salt fusion time periods of 48 hours or more. This further supports the inverse relationship between salt matrix continuity and tissue engineering scaffold continuity. Previous studies using solvent casting, particulate leaching processes in which salt is dispersed allow no control over pore interconnectivity in accord with the holes in pore walls displayed in the present study (Mikos, A. G., et al., "Preparation and characterization of poly(L-lactic acid) foams" *Polymer* 35:1068, 1994; Kaufmann, P. M., et al., "Highly porous polymer matrices as a three-dimensional culture system for hepatocytes" *Cell Transplant* 6:463, 1997; Murphy, W. L., et al., "Growth of continuous bone-like mineral within porous poly (lactide-co-glycolide) scaffolds in vitro" *J Biomed Mater Res* 50:50, 2000). In a recent study, investigators utilized heat to fuse polymeric porogen particles together prior to solvent casting (Ma, P. X. and Choi, J. "Biodegradable polymer scaffolds with well-defined interconnected spherical pore network" *Tissue Eng* 7:23, 2001). Although the use of heat may prove useful in several tissue engineering applications, the localized dissolution approach described herein may hold more broad applicability due to its potential for room temperature fusion of several types of porogen particle (both organic and inorganic), and its potential addition to processing techniques that include bioactive inductive factors (i.e., gas foaming/particulate leaching).

The fusion of NaCl crystals within PLG/NaCl mixtures prior to gas foaming also has a pronounced effect on pore structure. The pores within 24 hr of salt fusion (SF), gas foamed scaffolds appear to feed directly into one another, implying a very high interconnectivity without a large decrease in scaffold compressive moduli (see, for example, FIG. 6b). The gas foaming process has previously been used to process scaffolds containing biologically active vascular endothelial growth factor (Sheridan, M., et al., "Bioabsorbable polymer scaffolds for tissue engineering capable of sustained growth factor delivery" *J Control Rel* 64:91, 2000; Murphy, W. L., et al., "Sustained release of vascular endothelial growth factor from mineralized poly(lactide-co-glycolide) scaffolds for tissue engineering" *Biomaterials* 21:2521, 2000) and plasmid DNA encoding for platelet-derived growth factor (Shea, L. D., et al., "DNA delivery from polymer matrices for tissue engineering" *Nat Biotech* 17:551, 1999) to promote ingrowth of vascular tissue. Adding the novel salt fusion method of the present invention to the gas foaming and solvent casting methods has lead to the formation of a highly interconnected vascular supply throughout the interior of a tissue engineering scaffold. Achieving vascular ingrowth to maximum depths within a scaffold system is a substantial goal in bulk tissue engineering strategies, and the highly interconnected pore structure of the present invention is advantageous for optimal vascular tissue ingrowth.

When exposed to humid environments, adjacent salt crystals fuse in a process called 'caking', which often results in the formation of large agglomerations of rock salt or improperly stored table salt (anti-caking agents, such as calcium silicate, are added to table salt to prevent caking, essentially by absorbing moisture inside the package that otherwise would be absorbed into the surface of the salt particles). In a preferred embodiment, the present invention does not contemplate the use of anti-caking agents. The rate of diffusion of atoms within the solid salt crystal lattice is increased by the presence of absorbed water. The increased diffusion allows the surfaces of the contacting salt particles to coalesce, forming bridges between particles in a process similar to that used for solid sintering of non-vitreous ceramic materials. The individual particles begin to coalesce because, in the process, the total surface area of the salt particles is reduced, thus reducing the surface energy (Van Vlack, L. H. "Elements of Materials Science and Engineering," 4ed. Addison-Wesley Publishing Company, Reading, Mass., pp. 120 & 316, 1980). The increased sphericity of each particle of salt is also thermodynamically favored, since this also reduces the total surface energy of each particle.

D. Scaffold Molding

The solvent cast scaffolds had a significantly increased compressive modulus after 24 hours of salt fusion, whereas the gas foamed scaffolds did not. The solvent cast scaffolds the thicker struts of PLG material that were permitted to form in the space vacated by rounded corners and edges of the salt particles formed a stiffer structure, without an increase in the volume fraction of PLG in the scaffold. A similar increase in the modulus of the gas foamed scaffolds did not occur with increased NaCl fusion time. This may be due to the presence of PLG particles during the salt fusion in the gas foaming process. Undoubtedly there is some void space for interaction between adjacent NaCl crystals, even in the presence of both types of particles (NaCl and PLG). The displacement of the salt surface resulting from diffusion was restricted to movement within the available void space. Evidence in support of this is clear in FIG. 5 (b & d), in which the scaffold is composed of micro perforated sheets, not present in the solvent cast scaffold, suggesting that during the NaCl fusion process the moving salt crystal surface was obstructed by, and perhaps flowed around, the smaller PLG particles. Thus, although bridges were formed between adjacent salt particles, the movement of the crystal surfaces was constrained by the presence of the PLG particles. This may have prevented the growth of void spaces in the salt structure that would lead to the formation of thick-section struts in the PLG scaffold, explaining why there was increased pore interconnectivity, but not increased compressive modulus, in the gas foamed scaffolds.

E. Exemplary Applications

Although not limited to any particular application, the salt fusion method of embodiments of the present invention will be applicable to the engineering of neural and muscular tissues due to their dependence on pore interconnectivity. Regenerative processes in the bridging of neural tissue defects (axonal elongation) and the development of functional skeletal muscle tissue (myoblast fusion) are examples of physiological processes requiring intimate cell-cell interaction. Strategies to bridge nerve gaps using a variety of natural and synthetic scaffolding materials have been only moderately successful even in gaps less than 10 mm in length (Valentini, R. F., et al., "Collagen- and laminin-containing gels impede peripheral nerve regeneration through semipermeable nerve guidance channels" *Exp Neurol* 98:350, 1987; Aldini, N. N., et al., "Effectiveness of a bioabsorbable conduit in the repair of peripheral nerves" *Biomaterials* 17:959, 1996), and reasons for failure in many cases include lack of adequate pore interconnectivity and inadequate mechanical integrity of the conduit.

Recent studies using porous poly(lactic-co-glycolic acid) (Evans, G. R. D., et al., "Tissue engineered conduits: the use of biodegradable poly (D,L-lactic-co-glycolic acid) scaffolds in peripheral nerve regeneration" In: Stark, G. E., Horch, R., Tanczos, E., Eds. Biological Matrices and Tissue Reconstruction. Berlin: Springer, 1998, pp. 225-235) and poly(L-lactic acid) (Evans, G. R. D., et al., "In vivo evaluation of poly (L-lactic acid) porous conduits for peripheral nerve regeneration" *Biomaterials* 20:1109, 1999) scaffolds for neural regeneration have shown promise in 12 mm nerve defects in a rat sciatic nerve model. Extension of this basic concept to larger, critical nerve defects requires controlled pore interconnectivity to allow vascular ingrowth, avoid pruning of regenerating fibers during axonal elongation and ensure that elongating axons reach their target organs.

Enhanced and controlled pore interconnectivity are necessary scaffold characteristics to promote successful myoblast fusion. Further, the survival of cells within a functioning muscle organoid is diffusion limited (Dennis, R. G. and Kosnik, P. E., "Excitability and isometric contractile properties of mammalian skeletal muscle constructs engineered in vitro" *In Vitro Cell Dev Biol—Animal* 36:327, 2000) and thus ingrowth of vascular tissue is essential to increase the maximum diameter of functional muscle constructs in order to amplify contractile properties. Although not limited to any particular application, certain embodiments of the present invention (e.g., the salt fusion process) are particularly applicable in preparing highly interconnected scaffolds for neural and muscular applications. Although the present invention is not limited to any particular theory, the substantial advantages of pore interconnectivity in promoting three dimensional cell-cell interaction are believed to aid in the growth of neural and muscular tissue in tissue engineering scaffolds.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); L (liters); dl (decalitters); ml (milliliters); μl (microliters); cm (centimeters); mm (millimeters); μm (micrometers); nm (nanometers); ° C. (degrees Centigrade); RDA (representational difference analysis); nts (nucleotides); kV (kilovolts).

Example 1

In this example, NaCl frames and biodegradable polymer scaffolds are produced. The salt particles (Mallinkrodt, Paris, Ky.) were sieved to yield a range of sizes. NaCl crystals of a diameter of about 250-425 μm were used.

Porous scaffolds were prepared either by solvent casting/particulate leaching, or gas foaming/particulate leaching processes using NaCl as the particulate porogen. The solvent cast scaffolds were prepared essentially as described by Mikos, A. G., et al. ("Preparation and characterization of poly(L-lactic acid) foams" *Polymer* 35:1068, 1994; which is incorporated herein by reference). NaCl molds were made by subjecting NaCl crystals (diameter of about 250-425 μm) to 95% humidity for periods from 0-24 hr to achieve fusion of NaCl crystals prior to solvent casting. A closed, water-jacketed cell culture incubator (Forma Scientific, Inc.) held at 37° C. was used to create a 95% humidity environment for fusion of NaCl crystals.

Poly(lactide-co-glycolide) (PLG) pellets with a lactide:glycolide ratio of 85:15 were obtained from Medisorb, Inc. (intrinsic viscosity (I.V.)=0.78 dl/g) and Boehringer-Ingelheim Inc. (I.V.=1.5 dl/g). High inherent viscosity PLG was used in the solvent casting process to ensure that the scaffolds would retain adequate mechanical integrity despite their relatively high porosity (~97%). PLG pellets were dissolved in chloroform (Mallinkrodt, Paris, Ky.) to yield a solution of 10% weight/volume (w/v). The polymer solution was then poured into an NaCl-containing mold wherein the salt crystals had been fused, as described above. Following solvent evaporation, the salt was removed by immersion in distilled water for about 48 hours.

The gas foamed scaffolds were essentially prepared as described by Harris, L. D., et al. ("Open pore biodegradable matrices formed with gas foaming" *J Biomed Mater Res* 42:396, 1998; which is incorporated herein by reference). NaCl molds were made by subjecting NaCl crystals (diameter of about 250-425 μm) to 95% humidity for periods from 0-24 hr to achieve fusion of NaCl crystals prior to solvent casting. Following treatment in 95% humidity samples were dried in a vacuum desiccator for 48 hr before further processing. A closed, water jacketed cell culture incubator (Forma Scientific, Inc.) held at 37° C. was used to create a 95% humidity environment for fusion of NaCl crystals. PLG pellets (prepared as above) were dissolved in chloroform. Frames of fused NaCl were mixed with PLG were loaded into an aluminum die (1.35 cm diameter; Aldrich Chemical Co., Milwaukee, Wis.) and was compressed at 1500 Psi for 1 minute using a Carver Laboratory Press (Fred S. Carver, Inc., Menominee Falls, Wis.) to yield solid disks (thickness of about 3.4 mm). The samples were then exposed to high pressure $CO_2$ gas (800 psi) for 24 hours to saturate the polymer with gas. A theromodynamic instability then was created by decreasing the gas pressure to ambient pressure. This lead to the nucleation and growth of $CO_2$ pores within the polymer matrices. The NaCl particles subsequently were removed from the matrices by leaching the matrices in distilled water for 48 hours. All processing steps were performed at ambient temperature.

Scaffolds were circular disks with a diameter of about 12 mm and a thickness of about 3 mm. The pore size range was controlled by using NaCl particles with a diameter of about 250-425 μm in the processing. The total porosity of scaffolds was calculated using the known density of the solid polymer, the measured polymer mass of the scaffold, and the measured external volume of the scaffold.

Example 2

Figure 1B:
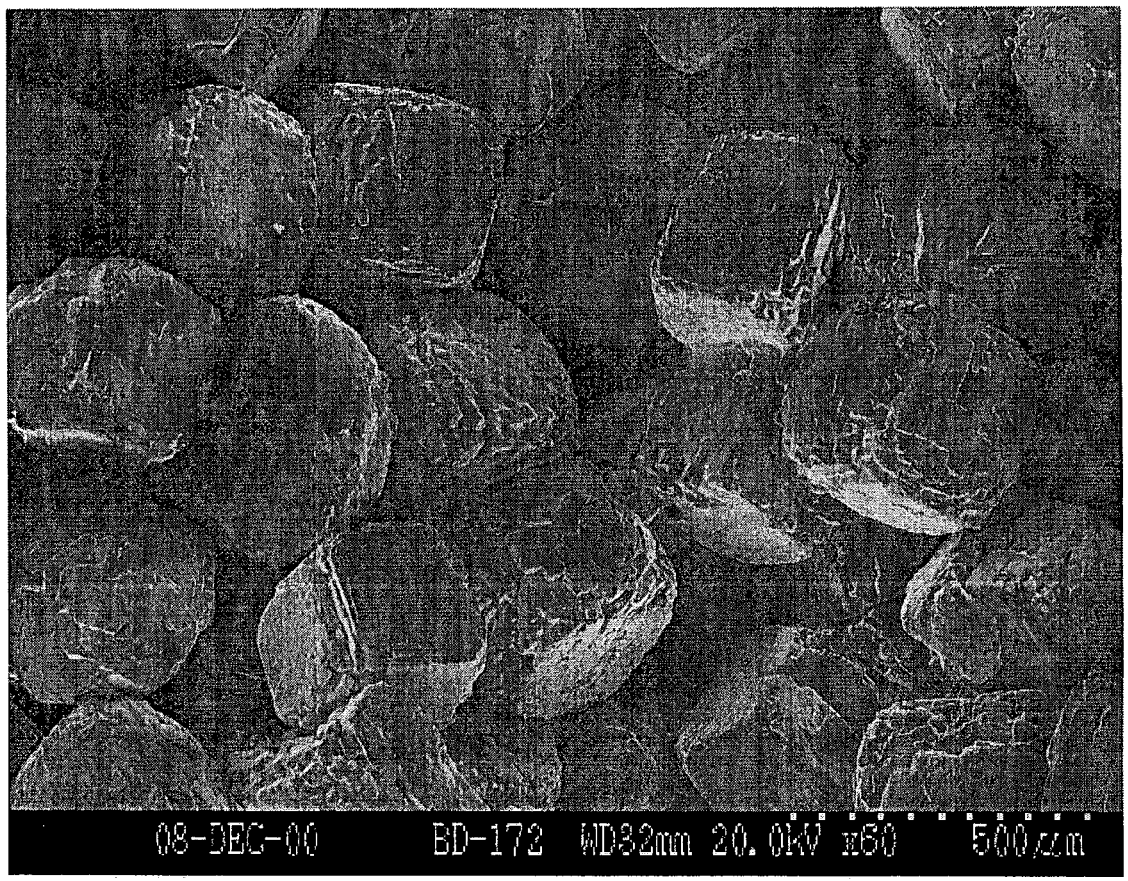
Figure 2A:
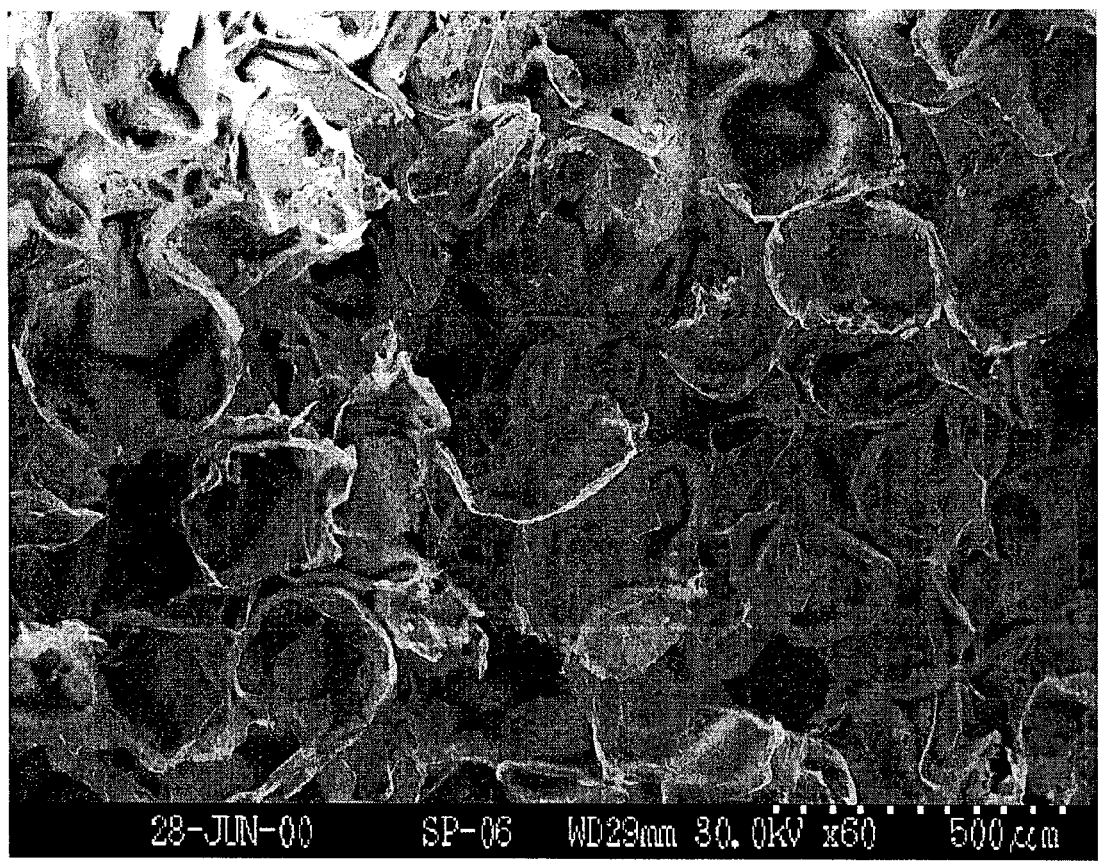
FIGS. 2a, 2b, 2c, 2d and 2e show electron micrographs of the cross section of solvent cast tissue engineering scaffolds prepared using the salt fusion process. One hour of slat fusion results in the presence of a low density of holes (31±10 μm diameter) in pore walls (A, C), while a 24 hour fusion treatment results in a high density of larger (78+21 μm) holes in pore walls (B, D). The 24 hour salt fused scaffolds also show contoured pore walls with a thick annulus directly adjacent to the interconnecting holes (B, D) that is particularly evident at higher magnification (E).
Figure 2B:
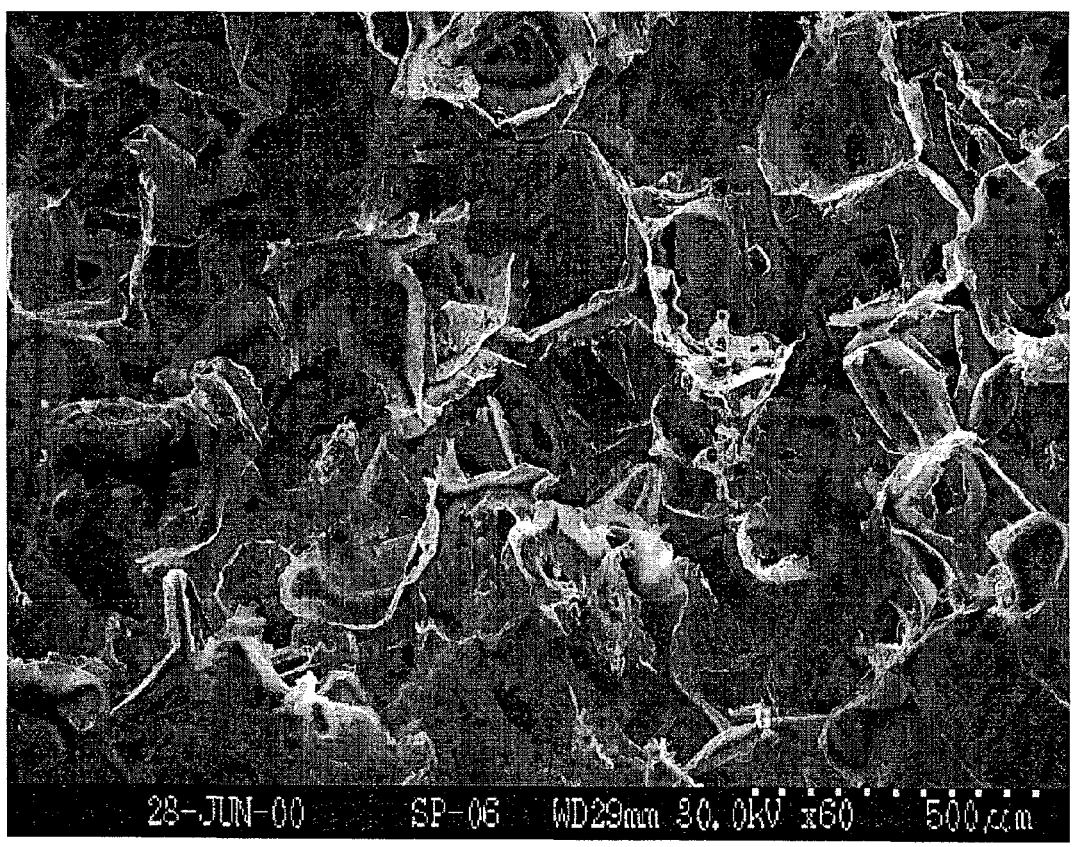
Figure 2C:
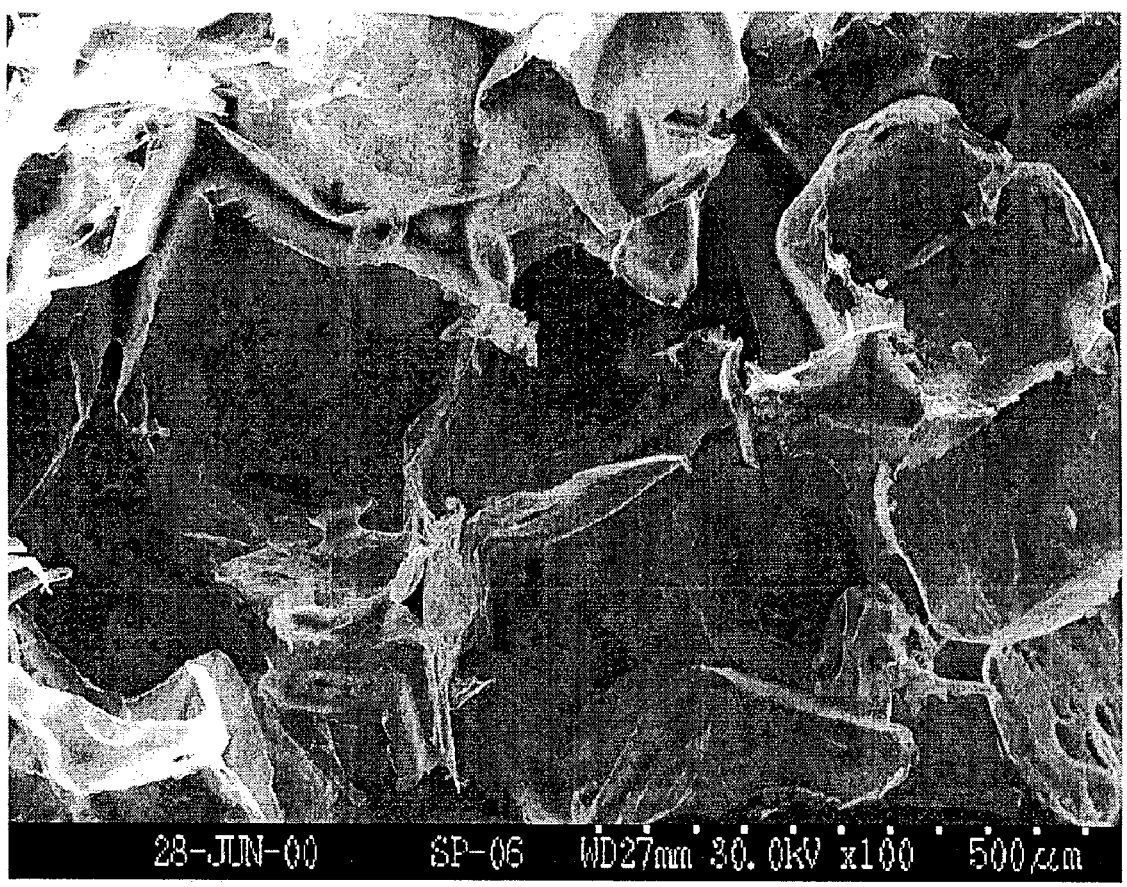
Figure 2D:
Figure 2E:
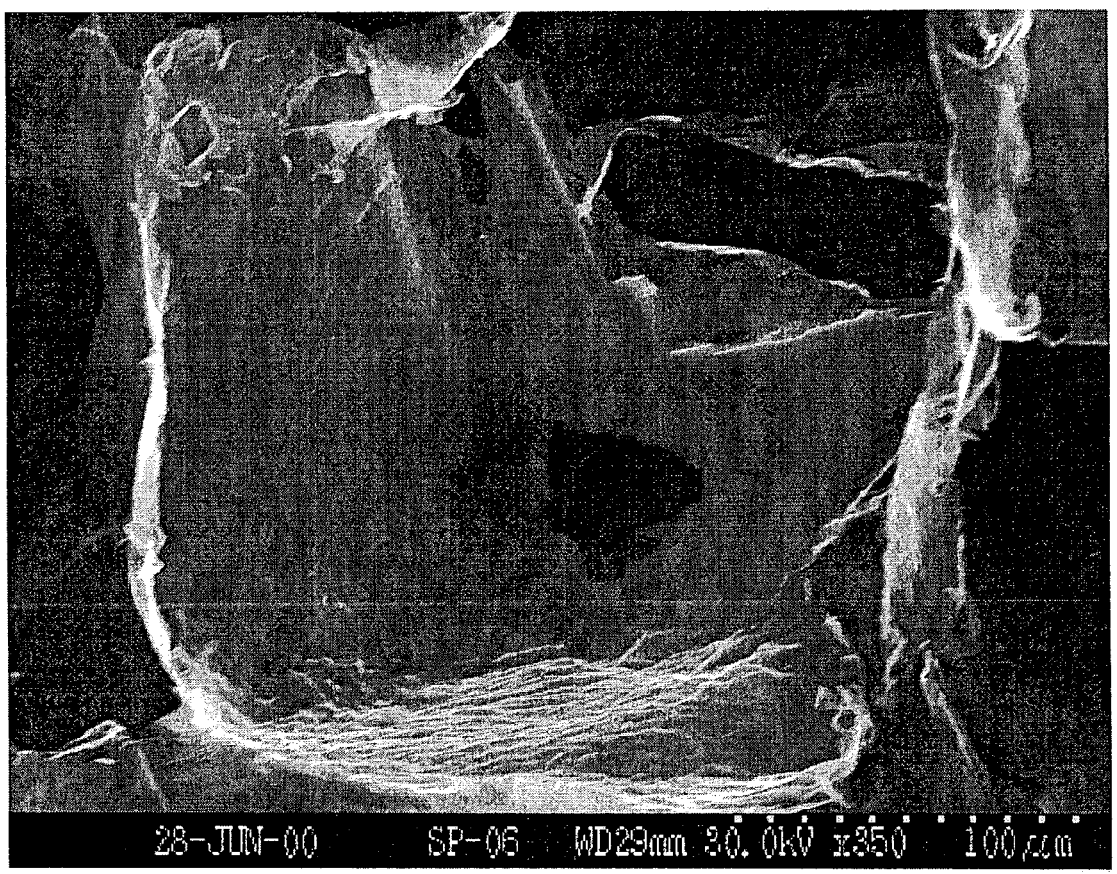

In this example, the scaffolds are characterized. Incubation of NaCl crystals in 95% humidity resulted in fusion of the crystals, creating a highly interconnected NaCl matrix (FIG. 1*a-b*). Fused salt molds were bisected and imaged prior to solvent casting to observe the extent of NaCl crystal fusion. In addition, polymer scaffolds were bisected after preparation via freeze fracture. A carbon coating was evaporated onto the surface of each bisected salt mold and polymer scaffold, and samples were imaged under high vacuum using a Hitachi S-3200N SEM operating at 20-30 kV. Fusion of salt crystals prior to addition of PLG in chloroform (solvent casting) resulted in enhanced pore interconnectivity within the scaffold. The pore structure within the scaffolds (FIG. 2) appears similar to the structure of the fused salt matrix (FIG. 1*a-b*), as expected. Pores within the cross section of 1 hr salt fusion (SF) samples display a defined pore structure with intermittent holes in pore walls, (FIG. 2*a*, 2*c*), while the cross section of scaffolds created from 24 hr SF samples display a much less organized pore structure and a very large density of holes in pore walls (FIG. 2*b*, 2*d*). The hole size increased significantly with fusion time, from an average diameter of 31±10 μm after 1 hour of fusion to 78±21 μm after 24 hours of fusion ($p<0.05$). In addition, the pore walls in the 24 hr SF scaffolds display thickness contours such that the walls appear thicker in the area adjacent to the holes in pore walls and along the outer diameter of the walls (FIG. 2*d*). A higher magnification view of a pore wall within a 24 hr SF scaffold further displays the contoured structure of the pore walls (FIG. 2*e*). The salt fusion process had no effect on the porosity of the scaffolds, and the calculated total porosities of the solvent cast scaffolds for each salt fusion time period were 97±1%.

Figure 3:
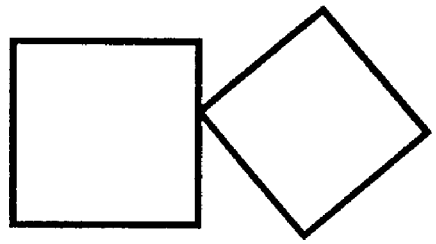
FIGS. 3a and 3b show the salt fusion process by solid diffusion in a solvent-enriched (about 95% humidity) atmosphere. (A) Prior to fusion, the salt grains have small areas of contact and sharp radii at edges and corners. (B) After 24 hours of exposure to 95% humidity, diffusion near the contact points had resulted in the formation of thick salt bridges between particles, as well as an increase in the radius of curvature at the edges and corners of each salt particle.
Figure 3:
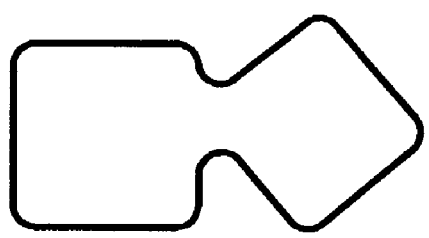
Figure 4:
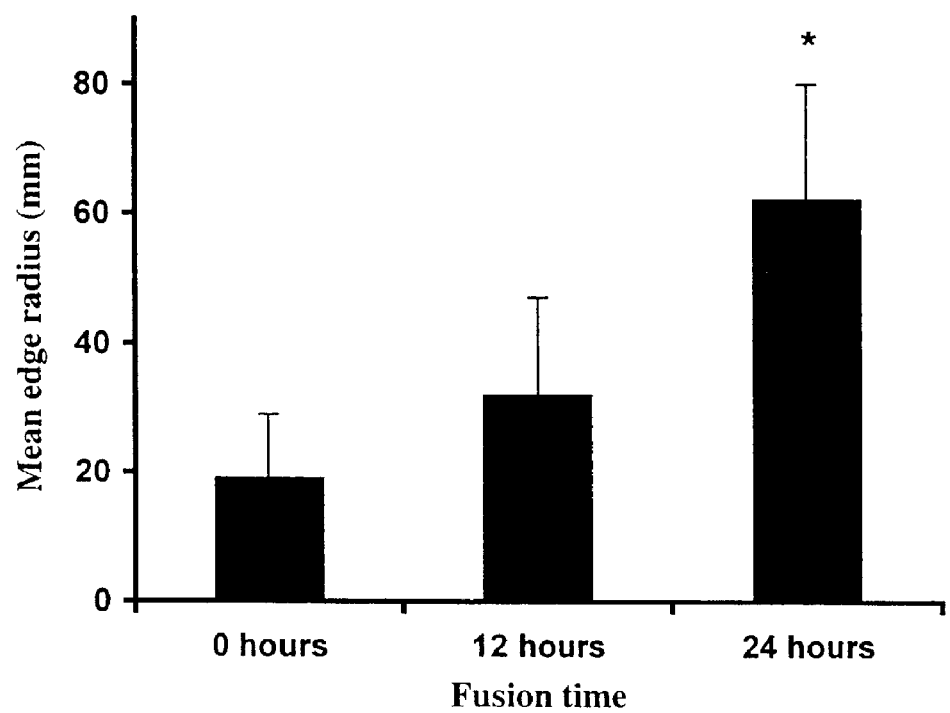
FIG. 4 shows an increase in the radius of curvature of salt crystal edges prior to addition of polymer in the solvent casting/particulate leaching method. Radii were measured from electron micrographs of salt crystals fused for 0, 12, and 24 hours. Based on an ANOVA followed by comparisons between group means (Bonferroni t tests), the change in mean edge radius from 0 to 12 hours was not significant ($p>0.05$), however, the change from 12 hours to 24 hours was extremely significant ($p<0.001$).

A close examination of the electron micrographs of the solvent cast scaffolds formed after 1 and 24 hours of NaCl fusion indicate that the exposure to 95% humidity has caused several important changes in the structure of the salt particles. In addition to the formation of bridges between particles at the points of contact, the radius of curvature of edges and corners in individual particles of salt has increased (FIGS. 1*a* and *b*). These changes are shown schematically (FIG. 3). The radius of curvature of salt crystals was calculated from electron micrographs using Microsoft™ Paint™ software. The pixel size for each image was calibrated, and the pencil tool was used to mark tangent points on crystal edges. The calibration values and pixel coordinates were then used to calculate the cord length between tangent points, which was multiplied by (⅔) to obtain the crystal radius of curvature. The diameter of holes in pore walls was determined by measuring the major and minor diametral axes of each hole using microsoft paint and taking the average. The increased radius of curvature at the edges and corners of each particle of salt results in an increased sphericity of each particle (FIG. 4), and thus in each resulting pore in the scaffold. The mean radius of curvature of the crystal edges increased from 19±10 μm, to 32±15 μm after 12 hours of exposure to 95% humidity, then to 62±18 μm after a full 24 hours of exposure (FIG. 4). As a result, many of the smaller crystals became nearly spherical in shape after 24 hours of fusion. One additional consequence is that thicker polymeric struts may be formed in the space vacated by the corners and edges of each salt crystal, which may result in the thickness contours in pore walls described above and in varied mechanical properties.

Figure 5A:
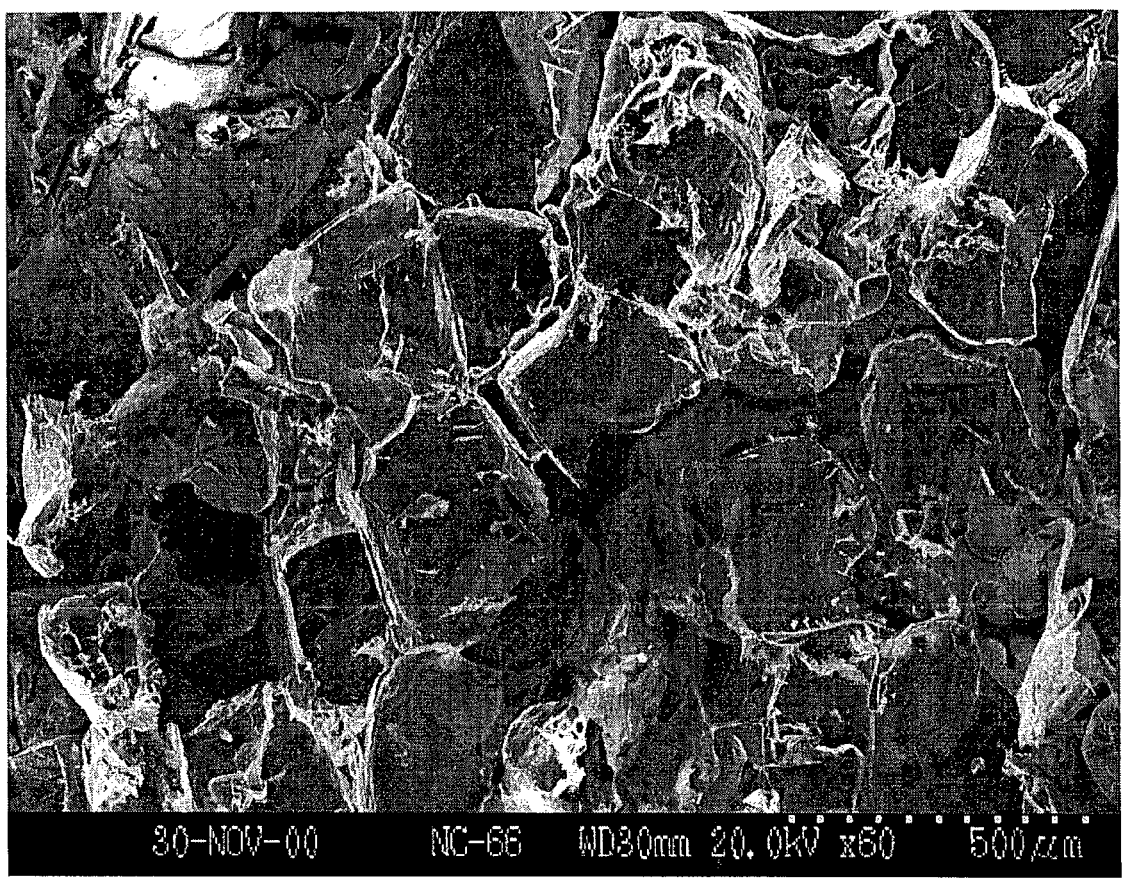
FIGS. 5a, 5b, 5c and 5d show electron micrographs of the cross section of gas foamed tissue engineering scaffolds prepared using the salt fusion process. One hour of salt fusion results in the presence of a few very small holes in pore walls (A, C) similar to those in the solvent cast scaffolds. The 24 hour salt fused scaffolds display a disorganized pore structure in which adjacent pores seem to feed into each other (B, D).
Figure 5B:
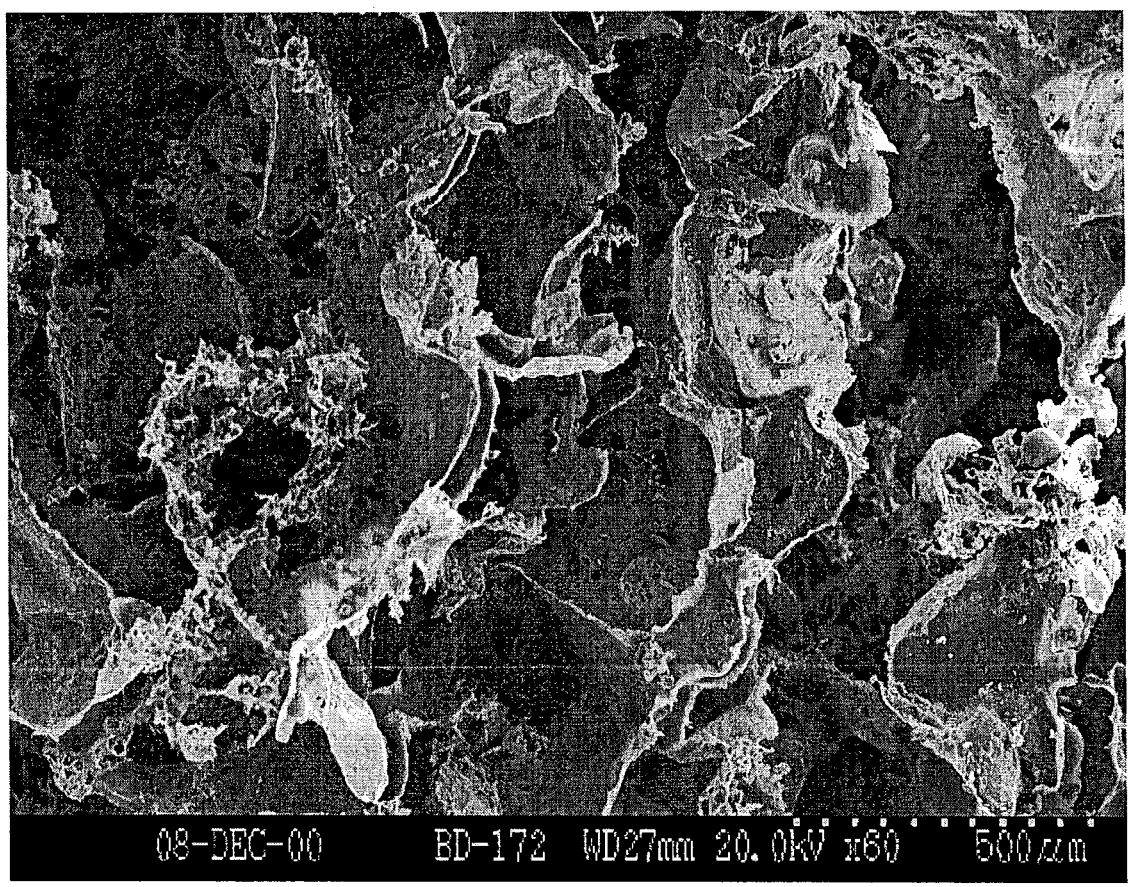
Figure 5C:
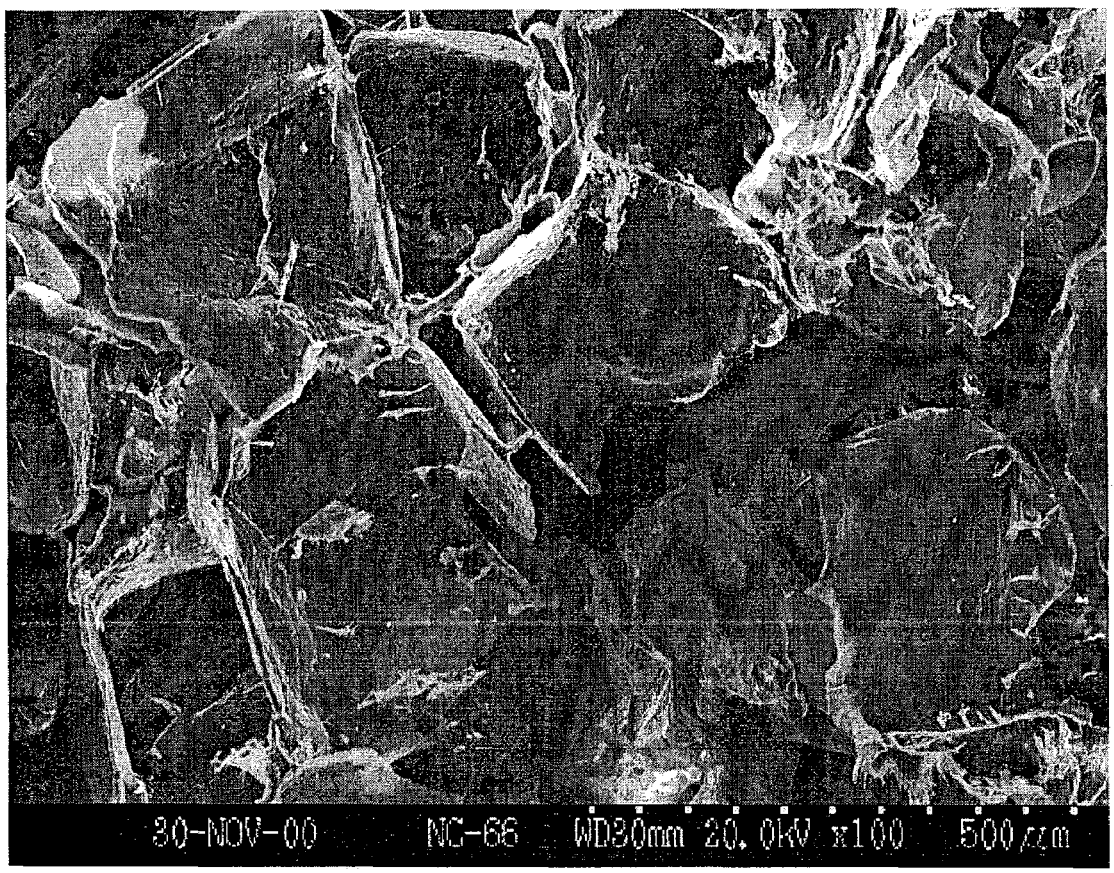
Figure 5D:
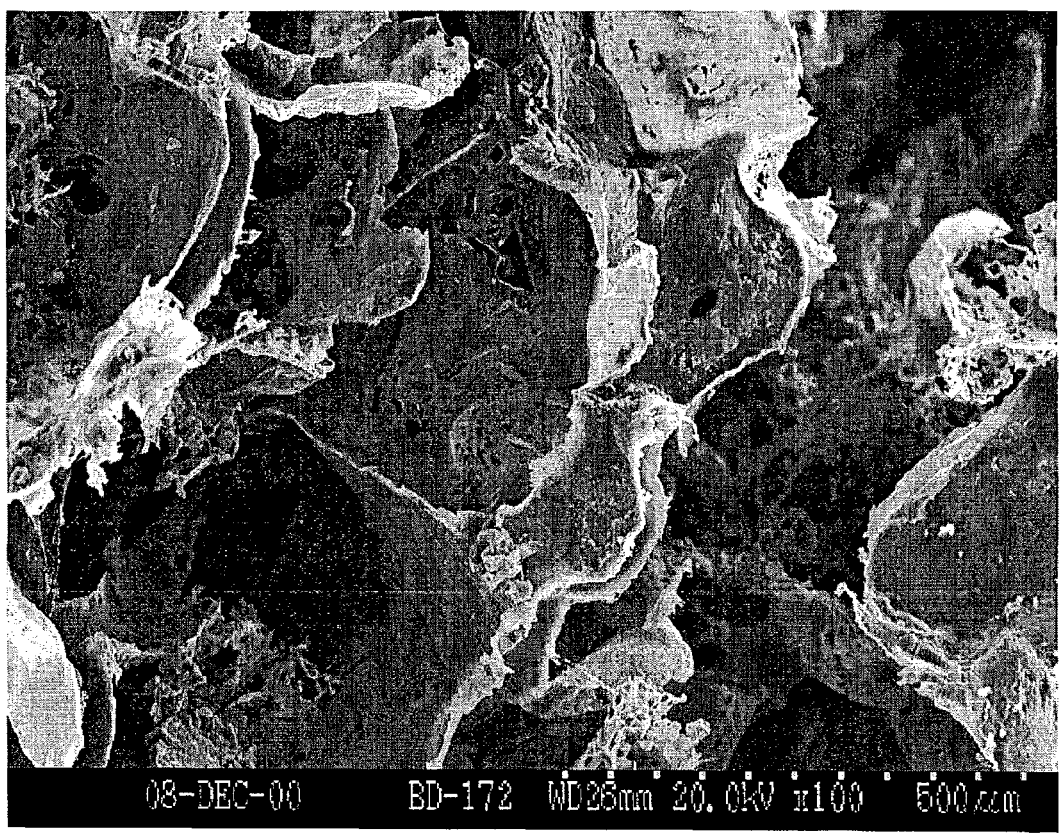

Fusion of salt crystals in PLG/NaCl pellets prior to gas foaming also resulted in a pronounced variation in pore structure. The cross section of 1 hr SF samples (FIG. 5a, 5c) shows small holes in pore walls similar to those in the solvent cast 1 hr SF samples. The 24 hr salt fusion samples lack a defined pore structure and pores appear to simply feed into each other (FIG. 5b, 5d). The gas foamed SF scaffolds do not display any of the contours in pore walls observed in the solvent cast SF samples. Again, the salt fusion process had no effect on the total scaffold porosity. The total porosities of the gas foamed scaffolds for each salt fusion time period were 94±1%.

Figure 6A:
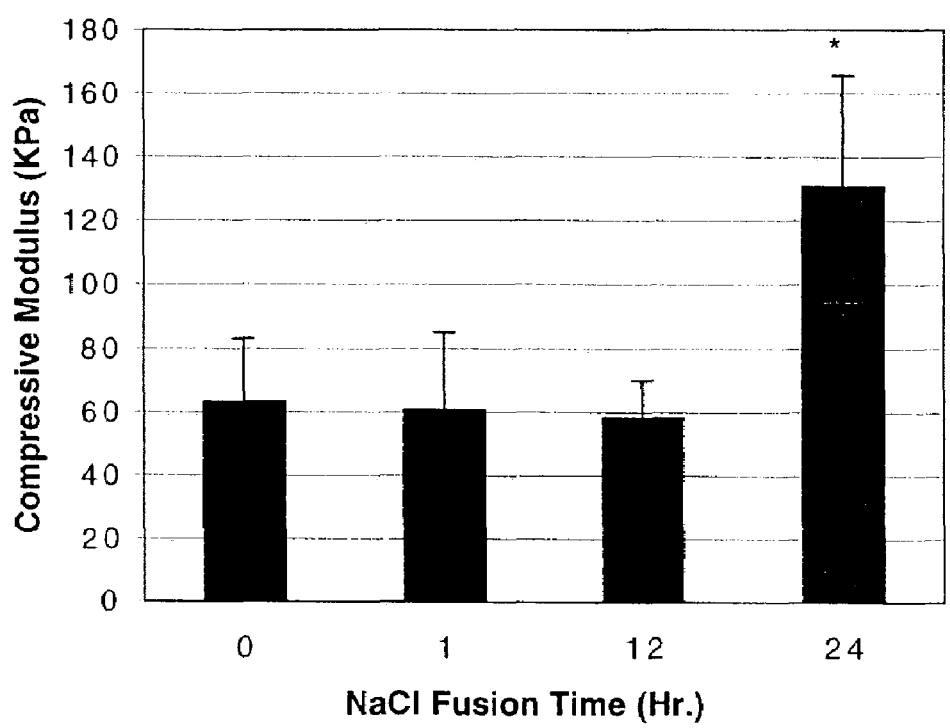
FIGS. 6a and 6b show compressive modulus of scaffolds subjected to salt fusion for various periods of time, and prepared via either solvent casting (a), or gas foaming (b). Values represent mean and standard deviation (n=4), and * indicates statistically significant difference relative to control ($p<0.05$).
Figure 6B:
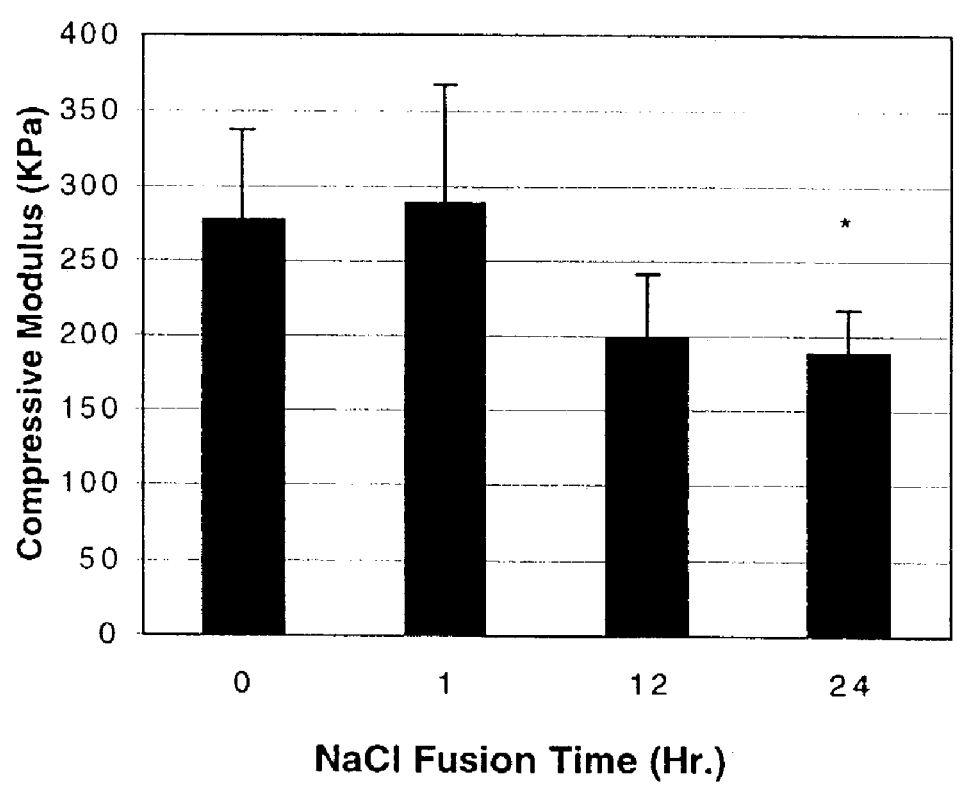

Fusion of salt crystals for 24 hr resulted in a 2-fold increase in the compressive modulus of the solvent cast scaffolds (FIG. 6a). Compressive moduli of scaffolds were determined using an MTS Bionix 100 mechanical testing system. Samples were compressed between platens with a constant deformation rate of 1 mm/min. Compression plates had a diameter of 45 mm, and thus covered the entire 12 mm diameter surface of the scaffold. A small pre-load was applied to each sample to ensure that the entire scaffold surface was in contact with the compression plates prior to testing, and the distance between plates prior to each test was equal to the measured thickness of the scaffold being tested. Compressive moduli were determined for scaffolds without salt fusion and for each of four samples for each salt fusion time. Values on graphs represent means and standard deviations. Statistical analysis was performed using InStat™ software, version 2.01. At each time point, experimental moduli were compared to control moduli via a Student's t-test to reveal significant differences in compressive modulus. No significant modulus change is observed after 1 hr, or 12 hr of salt fusion. Alternatively, there was a statistically significant decrease in the compressive modulus of gas foamed scaffolds processed using salt fusion when compared with control scaffolds (FIG. 6b).

Example 3

In this example, the scaffolds of the present invention are use for the culture of cells. The scaffold is sterilized by gamma radiation, ethylene oxide or cold sterilants. Cells are seeded on to the scaffold in an appropriate culture medium with any necessary growth factors, if needed. Cell culture media may be replaced by batch feeding or by perfusion methods. Sterility is maintained at all times.

Example 4

In this example, scaffolds of the present invention are used for the implantation of tissue into the body of test subjects. In other examples, scaffolds are used for direct implantation without tissue or cells to allow the conductive and inductive migration of cells from the body. Biopsies are taken form 16 mice. Biopsies are taken from any non-hemopoietic or hemopoietic tissue. Biopsies are taken from the same tissues source from all test animals. This example may be preformed on as many tissue types as desired. Cells are disassociated from basement membranes and syncytia by collagenase treatment. Cells from 8 of the mice are cultured in petri dishes. Cells from the other 8 mice are cultured on the scaffolds of the present invention. After culture of about 7 to 21 days, the cells or scaffolds with cells are implanted back into the respective mice. Follow up observation shows that the cell/scaffold implants of the present invention become invaginated with blood vessels and maintain a three dimensional structure. Follow up observation shows that the cells cultured without the scaffolds of the present invention dissipate into the host animal and do not become invaginated nor maintain a recognizable three dimensional structure. In examples where cells migrate into the scaffold from the surrounding tissues, follow up observation shows establishment of cells in the scaffolds with invagination of circulatory vessels.

As is evident from the foregoing, the present invention contemplates novel compositions and methods for the production of tissue engineering scaffolds. These novel compositions and methods allow for the efficient production of biocompatable structures of consistent pore size and interconnectivity.

The invention claimed is:

1. A method, comprising;
   a) providing
      i) a plurality of particles, said particles comprising a porogen comprising salt crystals and
      ii) a solution comprising a biocompatible polymer;
   b) exposing said porogen to between approximately 90%-100% humidity for a duration ranging between 1 hour-36 hours such that said porogen fuses together to produce a framework comprising a frame and free space between said fused porogen, wherein said free space increases as said duration increases;
   c) contacting said framework with said solution under conditions such that said solution fills greater than 75% of said free space;
   d) treating said solution such that said polymer forms a scaffold; and
   e) removing said fused porogen from said scaffold.

2. The method of claim 1, wherein said salt crystals are selected from the group consisting of calcium chloride, sodium chloride, sodium phosphate, potassium chloride, potassium phosphate, calcium phosphate and magnesium chloride.

3. The method of claim 1, wherein said polymer in said polymer solution is selected from the group consisting of a polyester, a poly(alpha-hydroxy ester), a polyether, a polystyrene and polymethylmethacrylate.

4. The method of claim 3, wherein said polyester is poly (lactide-co-glycolide).

5. The method of claim 3, wherein said polyether is polyethylene oxide or polyethylene glycol.

6. The method of claim 1, wherein said treating of step (d) comprises evaporating said polymer solution.

7. The method of claim 1, wherein said removing of step (e) comprises dissolving said fused salt crystals.

8. The method of claim 1, wherein said scaffold after step (e) comprises cells.

9. The method of claim 1, wherein said step b) additionally comprises exposing said porogen to positive pressure such that said free space between said fused porogen is controlled.

10. A method, consisting of:
a) providing
   i) a plurality of particles, said particles comprising a porogen comprising salt crystals and
   ii) a solution comprising a biocompatible polymer;
b) exposing said porogen to between approximately 90%-100% humidity for a duration ranging between 10 minutes-36 hours such that said porogen fuses together to produce a framework comprising a frame and free space between said fused porogen, wherein said free space increases as said duration increases;
c) contacting said framework with said solution under conditions such that said solution fills greater than 75% of said free space;
d) treating said solution such that said polymer forms a scaffold; and
e) removing said fused porogen from said scaffold.

11. The method of claim 10, wherein said salt crystals are selected from the group consisting of calcium chloride, sodium chloride, sodium phosphate, potassium chloride, potassium phosphate, calcium phosphate and magnesium chloride.

12. The method of claim 10, wherein said polymer in said polymer solution is selected from the group consisting of a polyester, a poly(alpha-hydroxy ester), a polyether, a polystyrene and polymethylmethacrylate.

13. The method of claim 12, wherein said polyester is poly(lactide-co-glycolide).

14. The method of claim 12, wherein said polyether is polyethylene oxide or polyethylene glycol.

15. The method of claim 10, wherein said treating of step (d) comprises evaporating said polymer solution.

16. The method of claim 10, wherein said removing of step (e) comprises dissolving said fused salt crystals.

* * * * *